United States Patent [19]

Rinaudo et al.

[11] 4,416,990

[45] Nov. 22, 1983

[54] ENZYMATIC CLARIFICATION PROCESS FOR IMPROVING THE INJECTIVITY AND FILTRABHILITY OF XANTHAN GUMS

[75] Inventors: Marguerite Rinaudo, Grenoble; Michel Milas, Eybens; Norbert Kohler, Le Chesnay, all of France

[73] Assignee: Institut Francais du Petrole, Rueil-Malmaison, France

[21] Appl. No.: 309,147

[22] Filed: Oct. 6, 1981

[30] Foreign Application Priority Data

Oct. 6, 1980 [FR] France ................................ 80 21395

[51] Int. Cl.³ ........................ C12P 19/06; C13L 3/00; C12R 1/645
[52] U.S. Cl. .................................... 435/104; 435/274; 435/911
[58] Field of Search ........................ 435/104, 274, 209

[56] References Cited

U.S. PATENT DOCUMENTS

| | | | |
|---|---|---|---|
| 4,010,071 | 3/1977 | Colegrove | 435/274 X |
| 4,032,663 | 6/1977 | Kobayashi et al. | 435/209 X |
| 4,094,739 | 6/1978 | Schroeck | 435/274 |
| 4,119,491 | 10/1978 | Wellington | 435/274 |
| 4,299,825 | 10/1981 | Lee | 435/104 |
| 4,326,037 | 4/1982 | Griffith et al. | 435/274 |

FOREIGN PATENT DOCUMENTS 2065688 10/1980 United Kingdom .

OTHER PUBLICATIONS

Barras et al., Advances in Chemistry Series, ACS Publication (1969), pp. 103–133.
Kohler et al., Society of Petroleum Engineers & Aime, SPE 7425 (1978), 7 pages.
Lipton, Society & Petroleum Engineers of AIME, SPE 5099 (1974), 16 pages.
Reese et al., Canadian Journal of Microbiology, vol. 5, (1959), pp. 173–185.
Rinaudo et al., Int. J. Biol. Macromol, Feb. 1980, vol. 2, pp. 45–48.

*Primary Examiner*—Nel M. Shapiro
*Attorney, Agent, or Firm*—Millen & White

[57] ABSTRACT

Enzymatic treatment, in aqueous dispersion, of a xanthan gum containing bacteria cell residues and microgels, as impurities, by means of Basidiomycete cellulase, the aqueous dispersion having a pH from 3 to 7 and containing at least 0.1 equivalent/liter of at least one salt of alkali or alkaline-earth metal, said treatment being conducted at a temperature from 25° to 65° C., improved the injectivity and filtrability thereof.

14 Claims, No Drawings

ENZYMATIC CLARIFICATION PROCESS FOR IMPROVING THE INJECTIVITY AND FILTRABHILITY OF XANTHAN GUMS

The present invention concerns an improvement to the injectivity and to the filtrability of xanthan gums in oil formations in view of improving the recovery of crude oil; it concerns more particularly a suitable treatment making use of a particular type of enzymatic system, to obtain limpid solutions of these xanthan gums whose injectivity and flowing properties through the oil formations do not result in a loss of intrinsic properties of the polysaccharide and particularly of its thickening power.

STATE OF THE ART

Xanthan gums are hydrophilic polysaccharides obtained by fermentation of suitable nutrients based on carbon hydrates, under the action of certain microorganisms, particularly bacteria of the Xanthomonas genus. Xanthan gum has numerous applications both in the food domain and in the petroleum domain. An important application consists of using xanthan gums for displacing oil from partially depleted crude oil reservoirs.

Attention has been paid during recent years to the fact that, by adding to the aqueous fluids injected for stimulating the oil production from oil formations, substances which increase their viscosity, it is possible to noticeably improve the enhanced oil recovery and thus, to significantly increase the amount of crude oil which can be extracted from a subterranean oil deposit during this operation. By selecting an injected solution containing a thickening agent at a sufficient concentration for imparting thereto a viscosity close to that of the oil to be displaced under the underground conditions, the natural tendency of water to flow through preferential paths is reduced and accordingly, the oil is more regularly displaced in a manner similar to that of a piston.

The xanthan gums constitute a particularly useful thickening agent. As a matter of fact, they are characterized by a high insensitivity to salinity and to the nature of the salts, in particular, they do not precipitate and their viscosity does not decrease in the normal conditions of use and also, they exhibit a high stability to mechanical stresses.

However, the xanthan gums also suffer defects, the more important of which consists of quickly clogging the oil formation in the immediate vicinity of the injection well, and thus preventing any flushing of this formation and, accordingly, any additional oil extraction or recovery.

This clogging or bad injectivity has many origins. On the one hand, the raw fermentation broths as well as the xanthan gums precipitated and separated from the fermentation broths, contain a certain number of insoluble particles issued from the fermentation step, such as bacteria cells or other cell fragments, which are difficulty separated from the fermentation juice or from aqueous dispersions of xanthan gums, essentially as a result of the very high viscosities thereof. On the other hand, the xanthan gum aqueous solutions, freed from the materials insoluble therein by means of various known techniques such as filtration at high pressure gradients through calibrated filters or through beds of diatomaceous earth, are also clogging at a relatively small distance from the injection well, where the pressure gradients become negligible and the flowing velocities are very low. As a matter of fact, the xanthan gum aqueous solutions still contain even after having removed the insoluble particles (clarification treatment), a certain number of translucent aggregates, deformable under the effect of the high stresses prevailing at the inlet of the formation at the vicinity of the injection well and which, over all, are not removable by mere filtration or centrifugation of these aqueous solutions. The presence of these aggregates, also called microgels, seems to be favored by inadequate conditions of isolation and precipitation of the powdered polysaccharide from the fermentation juice.

The injectivity tests used to evaluate the capacity of the raw solution of xanthan gum to penetrate into the first centimeters of the formation around the injection well are well known and the detailed conditions of these tests are described, for example, in the article of G. E. TINKER, R. W. BOWMAN and G. A. POPE: "Determination of In-situ mobility and wellbore impairment from polymer injectivity data" Journal of Petroleum Technology, May 1976, pages 586 to 596. One way of conducting the injectivity test consists of measuring, versus time, the accumulated volume of filtrate of the polysaccharide solution passing through a calibrated filter of a diameter of 47 mm or still of 142 mm and whose pore size ranges from 0.45 to 5.0 $\mu$m under a constant manometric pressure from 10 kPa to 300 kPa, thus simulating both the pore sizes of the formation around the injection well and the high pressure drops encountered therein.

The detection of the microgels present in the aqueous solution of xanthan gum may be effected by means of the so-called flowing or filtrability test as described in the article of N. KOHLER and G. CHAUVETEAU "Xanthan polysaccharide plugging behavior in porous media-Preferential use of fermentation broth" Journal of Petroleum Technology, February 1981, pages 349 to 358. This test is characterized by the injection at constant rate, by means of a double-action pump, of a clarified solution of xantan gum, through one or more calibrated filters of a pore diameter higher than 0.8 $\mu$m, for example filters with a pore diameter of 3 $\mu$m. This injection is preferably effected at rates corresponding to those encountered on the field, inside the formation typically lower than one meter per day. With the help of a differential pressure sensor, the pressure drops on both sides of the filter are recorded versus time for polymer solution and comparatively with the aqueous phase used for solubilizing the latter: $\Delta P$ polymer/$\Delta P$ water. This ratio of the pressure drop of the polymer solution as compared to that of water when circulated through the same porous medium (filters or natural porous media) is also called mobility reduction R$\lambda$. Another characteristic magnitude which is usefully controlled during such flowing of polymer solutions through porous media, consists of the relative viscosity $\eta$, ratio of the viscosity of the polymer solution to that of the dissolving water, whose value must not vary or only vary to a small extent during such flowing experiments.

A correct evaluation of the penetration and flowing capacity of a polysaccharide solution inside a petroleum formation must be made by means of one of the two above-mentioned tests, i.e. an injectivity test providing for the evaluation of clogging at the inlet of the formation by insoluble particles as well as a flowing or a filtrability test at constant flow rate for evaluating the clogging, if any, due to microgels at a certain distance from the injection well.

In the following detailed examples it suffices, in most cases, to proceed to a combined test consisting of passing the xanthan gum solution, before and after treatment with enzymes, through a 0.8 μm, Millipore filter, under a pressure 10 kPa, and to measure the accumulated volume of filtrate versus time.

These test conditions constitute a compromise between the injectivity test under high pressure, for checking the absence or presence of residual insoluble particles of a size greater than 0.8 μm, and the flowing test, under a lower pressure, for estimating the amount of microgels remaining in solution. A perfectly purified xanthan gum solution will then be characterized by the substantially perfect linearity of the accumulated filtrate volumes versus time.

Numerous suggestions have been made to avoid the limited conditions of use of the xanthan gum aqueous solutions and to improve their injectivity.

The U.S. Pat. No. 3,729,460 proposes a technique for improving the limpidity and injectivity of xanthan gum raw solutions by means of a chemical treatment with an alkaline solution, preferably in a pH range from 11.2 to 12.8 under high temperature (up to 120° C.). The use of strongly basic pH values is liable to lead to the conversion of the primary structure of the xanthan gum and to depolymerization. It has been established in article of D. LIPTON "improved Injectability of Biopolymer Solutions" preprint SPE No. 5099, presented at the 43$^{rd}$ annual meeting of the AIME Petroleum Engineer Society at Houston, TEXAS, 6–9 october 1974, that said treatment technique by means of a base did not improve the limpidity nor, consequently, the injectivity of the xanthan gum solutions.

The U.S. Pat. No. 4.010,071, No. 4,119,491, and No. 4,165,257 describe clarification processes for raw fermentation juices or aqueous solutions of xanthan gums with the use of an enzyme of the protease type. The treatment takes place preferably in a strongly basic medium (7.5 < pH < 13) and at temperatures lower than 60° C. A low salinity of the water and particularly a divalent ions content thereof lower than 100 ppm is recommended. Moreover, it is appropriate to filter, for example through diatomaceous earth, the so-treated xanthan gum solutions, to prevent injectivity losses resulting from the clogging of the formation by the imperfectly solvated protein-containing materials. This treatment by means of an enzyme of the protease type, although resulting in noticeable improvements as compared with untreated solutions, does not suffice to overcome, without further filtration, the clogging problems arising in the presence of insoluble inorganic or protein-free organic materials, and no mention is made of a possible effect of such enzymes of the protease type on microgels. On the other hand, the use of strongly basic pH values is also subject to the above-stated objections.

The U.S. Pat. No. 4,094,739 proposes to clarify Xanthomonas fermentation broths whose microbial cells have been first deactivated by pasteurization: a second fermentation with the use of a microorganism of the fungus type, solubilizes, in the presence of additional glucose, the residual Xanthomonas cells initially difficulty filtrable in view of their small size, by producing insoluble cells of a much larger size, more easily filtrable. This treatment consequently requires a preliminary filtration of said cells and nothing indicates to which extent the injectivity and filtrability of the obtained solutions are improved.

The U.S. Pat. No. 4,182,860 describes a clarification process consisting of solubilizing xanthan gum in a brine containing a minimum of 0.5% by weight of salt, followed with heating, at a temperature of at least 100° C., and with a further filtration, whereby is obtained a limpid solution. This process has the double disadvantage of requiring two steps, the filtration before the injection into the formation being indispensable, and of also resulting in a non-negligible risk of degradation of the xanthan gum as the result of the use, over a long time, of a high temperature and, consequently, in a loss of its thickening properties.

Finally, the British Pat. No. 2 065 688 describes an enzymatic method for improving the injectivity of polysaccharides; the enzyme used is an endoenzyme capable of hydrolyzing at least one of the bonds between the polysaccharide sugar units. The preferred enzyme is Rhizopus Arrhizius, a typical endoenzyme (cf. D. F. BARRAS and coll., in "Cellulases and their applications" of G. J. HAJNY and E. T. REESE, Advances in Chemistry series, ACS Publications, 1969, No. 95, pages 105–138, particularly page 119). No mention is made of an effect on microgels.

OBJECTS OF THE INVENTION

A first object of this invention is to provide a new method for clarification of aqueous solutions of xanthan gums, wherein the thickening power of these gums is maintained. Another object of this invention is to provide a method for clarification of the raw fermentation juice. Another object of the invention consists in the removal of the insoluble cell fragments produced in the fermentation process of these xanthan gums. Another object of the invention consists of improving the injectivity of xanthan gum solutions for their use in enhanced oil recovery. Still another object of the invention consists in the removal of microgels and hence in the improvement of the flowing properties of the xanthan gum solutions inside an oil formation at a certain distance from the injection well. Finally, another object of the invention consists in the use of solid compositions whereby during their dissolution in water, the limpidity, injectivity and flowing properties of said xanthan gum solutions are improved. Other objects of the invention will be made apparent from the following description thereof.

DESCRIPTION OF THE INVENTION

According to this invention it has been found that by treating, under specific conditions of salt concentration, an aqueous dispersion of xanthan gum by an enzyme or an enzyme mixture of the cellulase type produced by culture of a fungus pertaining to the class of Basidiomycetes, both the injectivity and the filtrability of the xanthan gum solutions are improved and limpid solutions are which can be used directly, after dilution at the desired concentration and viscosity, without any further treatment, as flushing fluid in oil formations.

These enzymes will be designated hereinafter as "polysaccharase of Basidiomycetes cellulase".

The enzymatic treatment of the invention is effected at a pH lower than 7, and, preferably, higher than 3, in aqueous medium having a concentration of dissolved salts of alkali and/or alkaline-earth metals of at least $10^{-1}$ equivalent/liter.

The temperature and the contact time are selected so as to be sufficient for obtaining the desired clarification without substantial viscosity decrease.

The polysaccharases of Basidiomycetes have a glucane hydrolase activity and, more specifically, a $\beta$-1,4-glucane glucanohydrolase or $\beta$-1,4-glucanase activity (E. T. REESE and M. MANDELS, Canadian Journal of Microbiology vol. 5, 1959, pages 173–185 and, particularly page 177). Accordingly, they are able to hydrolyze the main chain of the xanthan gum, known to be constituted of $\beta$-1,4-D-glucose recurrent units.

These enzymes are however used, according to the invention, under temperature and salt concentration conditions such that the xanthan gum properties themselves are not substantially affected, i.e. that no substantial viscosity decrease of the xanthan gum solution occurs.

Moreover, in view of the above reported state of the art, it is unexpected that the Basidiomycete polysaccharases, which constitute typical exo-enzymes (D. R. Barras and coll., above cited, page 116) provide for an improvement of the filtrability and injectivity of the xanthan gum solutions.

It is of interest to observe that the enzymes of the $\beta$ glucane exo-hydrolase type produced by culture of other fungi than those pertaining to the class of Basidiomycetes, particuarly fungi pertaining to the Aspergillus and Trichoderma types, have no effect comparable to that of the *Basidiomycete polysaccharases* on the xanthan gum solutions.

One of the advantages of the invention is that it is not necessary to purify the enzyme, the raw preparations being perfectly convenient.

Among the enzymes obtained from fungi of the Basidiomycetes type, those of the Agaricaceae and Polyporaceae families are particularly convenient and among the latter those of the Collybia, Lentinus, Pleurotus, Schizophyllum, Fistulina, Fomes, Polyporus, Poria and Trametes types. These fungi are also known by their QM number, recording number of the U.S. Army, Quatermaster Research and Engineering Center, Natick, Mass., for example QM 806, 807, 592, 594, 2378 etc . . . (cf Reese and Mandels, page 175).

The xanthan gums subjected to the treatment of the invention are, preferably, inactive gums, i.e. gums which have been subjected to a deactivation treatment of the Xanthomonas cells or other biologically active agents present in the culture medium at the end of the fermentation step, said treatment having for object to stabilize the xanthan gums and to protect them against subsequent biological attacks. This treatment, well known in the art, consists for example in a sterilization, pasteurization, acidification or chemical treatment, for example by means of formaldehyde, ethylene oxide, propylene oxide, $\beta$-propiolactone, glutaraldehyde or pivololactone and analogs.

The proportion of xanthan gum is, for example, from 0.01 to 3% and preferably from 0.04 to 1.5% by weight, with respect to water, and the enzyme proportion is, for example, from 0.001 to 0.5% by weight, preferably from 0.0025 to 0.05% by weight with respect to water, these proportions being not limitative. The minimum enzyme amount to be used is obviously dependent on the amount of active factor present in the selected preparation. Of course, and this is even preferable, the treatment by polysaccharase may be directly effected on the deactivated raw fermentation broth; in this case the enzyme is directly admixed with the raw fermentation broth or diluted with injected water, preferably containing from 0.04 to 1.5% by weight of xanthan gum, the mixture being then subjected to incubation. Moreover, when it is desired to store xanthan gums as powder without requiring any further clarification treatment for their dissolution in the oil-field water, this is easily achievable by first subjecting the fermentation broth to an enzymatic treatment and then proceeding to the precipitation and drying of the xanthan gum as powder, according to usual known techniques.

The obtained product may then be dissolved again, irrespective of the pH value, the temperature and the ionic strength of the dissolving water.

The Basidiomycete polysaccharase not only degrades the cell fragments and solid bacteria suspended in the xanthan gum solutions by converting them to hydrosoluble compounds, so as to finally obtain a limpid solution of xanthan gum, but also, and this is more surprising, the transluscent microgels responsible for the clogging of the oil formations at a certain distance from the injection well. In all of these operations of clarification and microgels removal, the thickening power of the xanthan gums is maintained. As is apparent, on the other hand, from the following detailed examples, the treatment by polysaccharases leads to limpid solutions of xanthan gum and to the improvement of both the injectivity and the flowing properties of said solutions, as shown by the corresponding tests through calibrated filters.

The Basidiomycete polysaccharase develops its maximum activity in a medium of acid pH, lower than 7 and higher than 3, advantageously a pH from 3 to 6. When the medium does not have the desired acidity, it may be imparted thereto by addition of an acid, for example hydrochloric acid, acetic acid or sulfuric acid.

The enzymatic treatment according to the invention takes place during an incubation period of, for example, from 0.5 to 60 hours, and preferably from 3 to 15 hours, at temperatures ranging from room temperature (25° C.) up to about 65° C., preferably from 40° to 60° C. Short treatment times are preferably associated with high temperatures and conversely. When it is desired to make use of the enzymatic treatment at higher temperatures, the optimum time will be short, for example 4 hours at 50° C., 1 or 2 hours at 60° C. The preferred temperatures range from 30° to 50° C. but must not however exceed the temperature beyond which the polysaccharase enzyme is liable to deactivate to a noticeable extent.

Stirring is not essential, but when this is possible, the aqueous solution containing the xanthan gum and polysaccharase is preferably stirred smoothly, continuously or periodically.

Another original feature of the invention is that the treatment by means of polysaccharase gives satisfactory results only when it is effected in the presence of water containing a sufficient concentration of dissolved salts. This minimum amount decreases with the temperature of the enzymatic treatment and it is accordingly difficult to give a very precise value thereof. It is at least $10^{-1}$ equivalent/liter and, in some cases at least 1 equivalent/liter.

The salts which are involved in the salinity calculation are mainly soluble salts of alkali or alkaline-earth metals. By way of example, the minimum of $10^{-1}$ equivalent/liter corresponds to $10^{-1}$ mole of NaCl or $0.5 \times 10^{-1}$ mole of $CaCl_2$ or of $Na_2SO_4$.

An attempted explanation of the mechanism of operation of the invention is as follows: it is known that xanthan gum in solution may have two different conformations in accordance with the total salinity and temperature of the solution: disordered conformation in distilled water or in water of low salinity (lower, for example, than $10^{-1}$ equivalents/liter for a temperature from about 25° to 40° C.), well-ordered conformation at higher salinities (higher than about $10^{-1}$ equivalent/liter in a temperature range which may extend much beyond the deactivation temperature of the enzyme). This conformational transition in accordance with the salinity and the temperature may be followed, for example, by measuring the rotary power $[\alpha]$ or, alternatively the reduced viscosity.

As has been recently shown (M. RINAUDO and M. MILAS "Enzymic hydrolysis of the bacterial polysaccharide xanthan by cellulase" Int. J. Biol. Macromol. 2 45-48, February 1980), the behavior of the xanthan gum in solution depends on its structure, which is in relation with the salinity and the temperature of the medium: in disordered conformation, the polysaccharase (glucane hydrolase) hydrolyses and degrades the polysaccharide whereas in well-ordered conformation, the degradation of said enzyme does not occur.

It was not to be expected, from the above paper, that by causing a *Basidiomycete polysaccharase* to act no longer on a purified polysaccharide but on an impure polysaccharide containing insoluble cell fragments and translucent microgels, it would be possible to obtain a selective attack on the fragments and microgels without concomitant attack of the xanthan gum.

The polysaccharase must be used in conditions of temperature and ionic strength such that the well-ordered structure is stable. An approximate value of the minimum salinity at each temperature and, conversely, of the maximum temperature for each salinity, can be obtained from the following empirical formula:

$$T^x = A + B \log \mu$$

where A and B are respectively of the order of 125 and 43 for a monovalent metal salt and $T^x$ (in °C) is the critical temperature not to be exceeded during the enzymatic treatment and $\mu$ is the ionic strength which takes into account both the contribution of the concentration in xanthan gum ($c_p$, expressed in equivalent per liter or mass concentration (g) divided by 622) and the external salt concentration ($c_s$ expressed in mole/l): $\mu = \Phi c_p + c_s$ ($\Phi$ is the dissociation degree of the xanthan gum, equal to 0.6 for monovalent ions). An empirical formula similar to the above one may also be deduced for divalent ions as well as for mixtures or monovalent ions with divalent ions. For the diluted polymer solutions at concentrations lower than 1 g/l, the polymer concentration will be omitted in the calculation.

The amount of dissolved salts required for carrying out the invention naturally exists in most of the oil-field waters and the clarification treatment by polysaccharase may thus be directly performed on the oil field by means of the oil-field water, without it being necessary to adjust the salinity. When, on the contrary, it is desired to proceed to the enzymatic treatment directly with the fermentation broth, for example at the outlet of the fermenter, this does not pose problems either since the fermentation broth contains a certain amount of nutritive salts necessary for the fermentation, the total salt content, which is variable according to the fermentation process, being usually higher than the minimum above-stated concentration.

Moreover, and this is also one of the pecularities of this invention, the treatment with polysaccharase is not greatly affected by the nature of the salts and in particular, the presence of divalent ions such as calcium and magnesium ions, imparting to water a certain hardness, is perfectly tolerated and has no indesirable effect on the enzymatic clarification process.

According to an additional feature of the present invention, solid compositions containing xanthan gum and Basidiomycete enzyme may be directly added to the oil-field water, removing thereby any requirement of separate addition of enzyme to the xanthan gum solution. These solid compositions have a particular interest when the enzymatic clarification must be achieved, for example, in situ, during an enhanced recovery operation. The enzymatic reaction will progress with the solubilization of the polysaccharide and, if the temperature is conveniently selected, the enzymatic clarification process will not extend the usual time required for the preparation of the injected xanthan gum solution.

It is thus possible to obtain a clarified solution having the desired viscosity, which may be directly used without any further treatment, particularly of filtration, and having injectivity and filtrability properties greatly improved for use in enhanced oil recovery operations.

This solid composition may contain, for example, from 1 to 100 and, preferably form 2 to 30 parts by weight of xanthan gum per part by weight of enzyme.

The following examples illustrate the invention but must not in any manner be considered as limited the scope thereof.

EXAMPLE 1

To 1 liter of raw fermentation broth of xanthan gum of industrial grade (Rhodopol 23 R, batch No. 430, of RHONE-POULENC INDUSTRIES Company, France), not filtered and containing, in addition to the active material (122 g of xanthan gum), insoluble Xanthomonas cells previously deactivated by thermal treatment as well as all the nutritive salts required for the fermentation (about 5 g/l of alkali and alkaline-earth metal salts), there is first added 400 mg of sodium azide as bacteriostatic agent, so as to prevent the bacterial degradation of the polysaccharide, as well as a small amount of hydrochloric acid to bring the pH of the broth solution to a value of 5, before adding 500 mg of Basidiomycete polysaccharase, Poria genus. This exo-enzyme is allowed to act for 48 hours at 50° C., the pH is then brought back to 7 and the obtained limpid solution is diluted to a concentration of 400 mg/l of polymer by means of water containing 20 g/l of NaCl.

On the obtained solution, there is first effected a rapid filtration test consisting of passing the obtained solution, under a charge of 10 kPa, through a Millipore filter of 0.8 $\mu$m ($\Phi = 47$ mm) and measuring the accumulated volumes of filtrate versus time. The results of table 1 show that the filtrability of the broth treated with enzymes is strongly improved as compared to that of the untreated raw broth (about 25 cc of accumulated volume of filtrate after 30 minutes of filtration under the same conditions).

In order to complete this qualitative test, a further comparative flow test is conducted at constant rate (q=3 cc/h, v=0.25 m/j, t=30° C.) through Millipore filters of 3 $\mu$m ($\Phi = 21$ mm) arranged in series, contained in two filter supports (Table 2). It is observed that the broth treated with enzyme has no clogging effect on the two filter systems in series; a constant and low value of the ratio of the pressure drops (Δp pol=pressure drop for the polymer solution; Δp water=pressure drop for pure water) is rapidly obtained. The untreated raw broth, on the contrary, results in a substantial clogging of the inlet filter, essentially due to the presence of insoluble particles in suspension, and a low and progressive clogging of the following filters which may be attributed to the effect of the microgels. A viscosity decrease (Δη is also observed during the passage of the untreated raw broth through the filters, this being not the case with using the broth treated with enzymes.

The treatment of the raw fermentation broth with Basidiomycete polysaccharase thus results not only in the almost complete disappearance of the particles in suspension, but also in the dissolution of the microgels. Moreover, during the enzymatic treatment, the viscosity of the fermentation broth remains constant, indicating that the enzyme has not degraded the xanthan gum. This may be attributed to the fact that, as a result of a salinity higher than $10^{-1}$ equivalents/liter of dissolution water, the xanthan gum must normally be in the well-ordered conformation in the raw broth (cf. Rinaudo and Milas, above cited).

TABLE 1

Filtrability test on a raw fermentation broth treated with Basidiomycete polysaccharase.

| TIME IN MINUTES | ACCUMULED VOLUME OF FILTRATE IN cm$^3$ |
| --- | --- |
| 5 | 144 |
| 10 | 264 |
| 15 | 368 |
| 20 | 450 |
| 25 | 510 |
| 30 | 550 |
| 35 | 574 |

TABLE 2

Comparative flowing tests on a broth treated with enzymes and on an untreated raw broth.

| INJECTED VOLUME (cc) | BROTH TREATED WITH ENZYMES | | | UNTREATED RAW BROTH | | |
| --- | --- | --- | --- | --- | --- | --- |
| | $\frac{\Delta P_{pol}}{\Delta P_{water}}$ (1) | $\frac{\Delta P_{pol}}{\Delta P_{water}}$ (2) | Δ η in % | $\frac{\Delta P_{pol}}{\Delta P_{water}}$ (1) | $\frac{\Delta P_{pol}}{\Delta P_{water}}$ (2) | Δ η in % |
| 50 | 8.4 | 8.1 | 0 | 210 | 14 | 13 |
| 100 | 9.5 | 9.4 | 0 | 520 | 22 | 8 |
| 150 | 10.7 | 10.5 | 0 | 600 | 31 | 8 |
| 200 | 10.8 | 10.5 | 0 | 640 | 72 | 7 |

(1) inlet filter of 3 μm
(2) 3 following filters of 3 μm.

EXAMPLE 2

Aqueous dispersions of powdered polysaccharide Rhodopol 23 R, batch No. 79-123-1, of RHONE-POULENC INDUSTRIES COMPANY have been made in waters of different salt contents, at a concentration of 1600 mg/l. After having brought to 5 the pH of the different solutions, 500 mg/l of the enzyme of example 1 is added and the treatment is performed at a temperature of 43° C. for variable times (Table 3). At the end of various enzymatic treatments each of these solutions has been brought to a pH of 7 and diluted at Cp=400 ppm with the corresponding water amount, before subjecting each solution to the quick filtrability test through a Millipore filter of 0.8 μm (φ=47 mm) under 10 kPa.

From table 3 it is observed that the filtrability, after treatment with polysaccharase, does not vary substantially for waters having respective salinities of 5 g/l and 20 g/l of NaCl, that the treatment with Basidiomycete polysaccharase is also efficient in oil-field water, although with longer treatment times, and that the filtrability is not substantially improved by an enzymatic treatment with protease, alcalase at pH 9, in water containing 20 g/l of NaCl (Table 3, last column).

The enzymatic treatment according to the invention consequently provides for an improvement of the filtrability of the xanthan gums in a powdered form.

TABLE 3

Enzymatic treatments at different values of ionic strength

| | accumulated volumes in cc | | | |
| --- | --- | --- | --- | --- |
| time in minutes | 5 g/l NaCl pH 5 4 h | 20 g/l NaCl pH 5 4 h | oil-field water* pH 5 24 h | 20 g/l NaCl alcalase pH 9 6 h |
| 5 | 145 | 150 | 165 | 4 |
| 10 | 285 | 300 | 315 | 7 |
| 15 | 420 | 440 | 475 | 11 |
| 20 | 550 | 575 | 650 | 14 |
| 25 | 680 | 700 | 775 | 17 |

*Composition of the oil-field water: 8600 ppm of sodium ions, 1300 ppm of calcium ions and 290 ppm of magnesium ions for a total salinity of about 30 g/l.

EXAMPLE 3

This example is destined to show the advantage of using enzymes of the Basidiomycete type as compared with other enzymatic preparations, consisting either of polysaccharases or proteases (P). For this purpose, dispersions at 1600 mg/l of a powdered saccharide Rhodopol 23 R, batch No. 80-269, of RHONE-POULENC INDUSTRIES Company have been prepared in water containing 20 g/l of NaCl and treated with 500 ppm of various enzymatic preparations, at a pH corresponding to the maximum of activity. At the end of the thermal treatment (43° or 50° C.), the obtained solutions have been brought to pH 7 and diluted at Cp=400 ppm with water containing 20 g/l of NaCl before being tested.

Table 4 summarizes, for each enzymatic preparation, the treatment conditions, as well as the accumulated volumes of filtrate through a Millipore filter of 0.8 μm under 10 kPa, obtained after 35 minutes of filtration.

TABLE 4

Compared activities of polysaccharases (PS) and proteases (P)

| ENZYME | TYPE (PS or P) | TREATMENT CONDITIONS | | | ACCUMULATED VOLUME OF FILTRATE IN cm$^3$ (35') |
| --- | --- | --- | --- | --- | --- |
| | | pH | T °C. | TIME (h) | |
| Basidiomycete g. Polyporus | PS | 5 | 50 | 22 | 104 |
| Basidiomycete | PS | 5 | 43 | 16 | 130 |

TABLE 4-continued

Compared activities of polysaccharases (PS) and proteases (P)

| ENZYME | TYPE (PS or P) | TREATMENT CONDITIONS pH | T °C. | TIME (h) | ACCUMULATED VOLUME OF FILTRATE IN cm³ (35') |
|---|---|---|---|---|---|
| g. Trametes | | | | | |
| Aspergillus niger | PS | 5 | 50 | 22 | 10 |
| Aspergillus niger | PS | 5 | 50 | 22 | 12 |
| Trichoderma reesei | PS | 5 | 50 | 22 | 7.5 |
| Basic protease | P | 9 | 43 | 22 | 18 |
| Neutral protease | P | 7 | 50 | 22 | 10.5 |
| Acid protease | P | 6.5 | 43 | 23 | 17 |
| Bacillus subtilis | PS | 7 | 50 | 22 | 11.5 |

It is observed that the activity of the polysaccharases according to the invention is about 10 times that of the other polysaccharases or of proteases. Particularly, it can be seen that the polysaccharases of *Aspergillus niger* and *Trichoderma reesei* which are known to have a β1.4 glucane exo-hydrolaser activity, do not provide for an improvement of the filtrability of xanthan gum as powder in water of selected salinity as is the case with Basidiomycete exo-enzymes. These Aspergillus niger and Trichoderma reesei polysaccharases have no significant effect on the microgels of the polymer in spite of the fact that the water salinity is higher than $10^{-1}$ M/l.

EXAMPLE 4

This example is destined to show the specific action of the polysaccharases according to the present invention on the microgels contained in a xanthan gum in powder form. For this purpose there was first prepared a 400 mg/l dispersion of Xanflood xanthan gum powder, batch No. 14 630 of Kelco Company, U.S.A., in water containing 20 g/l of NaCl and 400 mg/l of $NaN_3$. This solution was then clarified by filtration according to a standard method (Millipore filters of 3 μm and then 0.8 μm under 100 kPa) in order to remove the insoluble particles and make it limpid.

A portion of the obtained limpid solution was treated with 500 mg/l of an enzymatic preparation obtained from Basidiomycete, Polyporus genus. After 120 hours of treatment at 43° C. and at a pH of 5, the pH of the solution was brought to 7 and a flowing test was then conducted at constant rate (q=3 cc/h) for the two solutions through Millipore filters of 3 μm (φ=21 mm) arranged in series.

Table 5 gives comparative results, at various flow rates and thus at various velocity gradients, of the mobility reduction values $$\left( R\lambda = \frac{\Delta p\ pol.}{\Delta p\ water} \right)$$

For the solution merely clarified by filtration (containing all the mirogels) and the solution further subjected to an enzymatic treatment according to the invention. It must be observed that the mobility reduction value depends, on the one hand, on the microgel content of the solution and, on the other hand, on the velocity gradient $\mathring{\gamma}$.

In Table 5 there is observed a substantial difference, practically independent from the flow rate of the polymer solution through the filters, between the solution merely clarified by filtration and that additionally subjected to an enzymatic treatment. The latter has removed practically all the microgels from the xanthan gum solution.

TABLE 5

Removal of microgels by enzymatic treatment.

$$R\lambda = \frac{\Delta p\ pol}{\Delta p\ water}$$

| q cm3/h | $\mathring{\gamma}$ sec$^{-1}$ | SOLUTION BEFORE TREATMENT WITH ENZYMES | SOLUTION AFTER TREATMENT WITH ENZYMES |
|---|---|---|---|
| 3 | 8.85 | 502 | 6.07 |
| 6 | 17.7 | 240 | 5.35 |
| 11.25 | 33.2 | 158 | 4.79 |
| 15 | 44.3 | 131 | 4.58 |
| 27 | 79.7 | 92.7 | 4.10 |

EXAMPLE 5

The zanthan gum contained in the fermentation broth of example 1 and which has been subjected to the treatment with the polysaccharase of the same example, is precipitated with 50% ethyl alcohol. The precipitate is then washed with pure isopropyl alcohol, then dried under vacuum for 2 days in a vacuum drier at 50° C.

The so-isolated polysaccharide is again dissolved at a concentration of 0.4 g/liter in water containing 20 g/l of NaCl and 30 ppm by weight of Kathon (a Rohm and Haas bactericide). The obtained limpid solution is then subjected to the quick filtrabilty test by passage, under a charge of 10 kPa, through a Millipore filter of 0.8 μm. No clogging is observed; the filtrate volume per time unit is substantially constant on 1 liter and the viscosity of the mother solution is entirely maintained in the filtrate.

This result shows that after treatment with a Basidiomycete polysaccharase, the improvements of the clarification and also of the filtrability, observed for the fermentation broth, are also observed in the polysaccharide separated as powder from said broth. Under the same experimental conditions, the xanthan gum, isolated as powder from a raw broth not treated with enzymes, always has a clogging effet.

EXAMPLE 6

This example is destined to determine how accurately, for a given temperature of the enzymatic treatment (38° C.), the salinity limits for which the viscosity of the xanthan gum is not affected or, likewise, the salinity limit for a given temperature at which the xanthan gum is in well-ordered conformation.

A solution of 0.4 g/l is prepared from xanthan gum powder (Rhodopol 23 R, batch No. 79-123-1, RHONE-POULENC INDUSTRIES, FRANCE) in waters of different NaCl contents:

A: distilled water; B: $3.5 \times 10^{-3}$M; C: $7 \times 10^{-3}$M; D: $10^{-2}$M; E: $10^{-1}$M.

All the so-prepared solutions are turbid and are subjected to a preliminary clarification treatment by filtration through calibrated filters (3 μm and then 0.8 μm/100 kPa).

To each of these solutions, there is added 0.1 g/l of the polysaccharase obtained from Basidiomycete Poria genus and the enzyme is allowed to act at a temperature of 38° C.

The viscosity measurement versus time (0<t<2000 seconds) of these different solutions shows an abrupt drop for solutions A, B and C, a positive but slower decrease for solution D and no viscosity variation for solution E, even when the treatment with polysaccharase is continued for 48 hours at 38° C.

These results clearly indicate that below a NaCl content of $10^{-1}$M (about 5.8 g/liter), a temperature of 38° C., the xanthan gum strongly hydrolyzes, and this may be attributed to the fact that it would then have, in solution, a disordered conformation making possible the hydrolysis and, consequently, the degradation of the polysaccharide by the polysaccharase.

The experimental conditions of solution E ($10^{-1}$M of NaCl, 0.4 g/l of polymer 0.1 g/l of polysaccharase, t° = 38° C.) have been reproduced, except however the resultant solution was not prelimiarily clarified by filtration. It is observed, after about 24 hours at 38° C., that the solution becomes limpid and the measured viscosity shows that the thickening powder was not effected.

This result shows that above the salinity limit, not only is the xanthan gum not hydrolyzed but, on the contrary, the polysaccharase progressively clarifies the solution when the xanthan gum is in a well-ordered conformation.

EXAMPLE 7

Two solid compositions, each containig 1.6 g of xanthan gum Rhodopol 23 R, batch No. 80-269, RHONE-POULENC INDUSTRIES, FRANCE, 500 mg of polysaccharase obtained from Basidiomycete Poria and 400 mg of NaN$_3$, are first prepared. Each of these solid compositions is dispersed in one liter of water at pH 5 containing 20 g of NaCl. Simultaneously with the dissolution of the polymer, the enzymatic treatment is effected while varying only the temperature and the treatment time: A: 12 hours at 43° C., B: 30 hours at 30° C. A reference solution C which contais 1.6 g/l of xanthan gum and 0.4 g/l of NaN$_3$ is also prepared.

It is observed that solutions A and B become progressively limpid whereas the reference solution C remains opaque. At the end of the treatment by polysaccharase, the various solutions, brought to pH 7, are subjected to an injectivity test by passing them, under a constant charge of 10 kPa, through a Millipore filter of 0.8 μm (diameter 142 mm). Table 6 indicates the accumulated volumes of filtrate obtained versus time for solutions A and B as compared with the reference solution C.

It is observed that both solutions A and B have a clearly improved filtrability as compared with the initial solution and that the use of a solid composition according to the present invention does not seem to affect either the dissolution of the polymer or the treatment by polysaccharase.

TABLE 6

Comparative filtrability of solid xanthan gum enzyme compositions

| SOLUTION | FILTRATE ACCUMULATED VOLUME (cc) TIME in MINUTES | | | | | | | |
|---|---|---|---|---|---|---|---|---|
| | 10 | 20 | 30 | 40 | 50 | 60 | 70 | 80 |
| A (12 h at 43° C.) | 33 | 62 | 85 | 106 | 125 | 142 | 158 | 173 |
| B (30 h at 30° C.) | 21 | 45 | 67 | 89 | 109 | 128 | 146 | 162 |
| C (reference) | 10 | 17 | 24 | 29 | 33 | 36 | 40 | 43 |

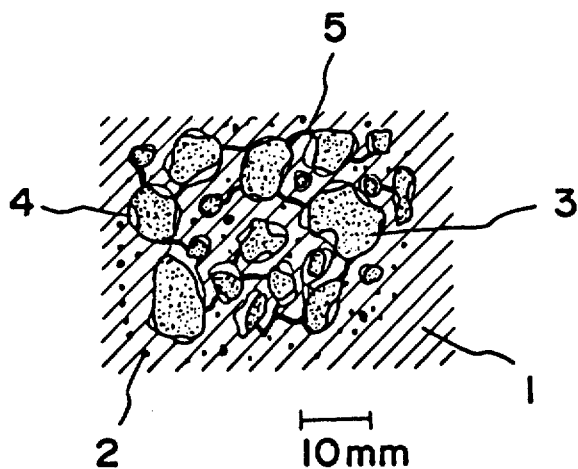

What is claimed:

1. A process for enzymatically purifying, an impure xanthan gum containing, as impurities, at least one of bacterial cell residues or microgels, which comprises contacting an aqueous dispersion of said impure xanthan gum with a polysaccharase enzyme preparation of Basidiomycetes Polyporaceae cellulose, said aqueous dispersion having a pH from 3 to 7 and a total concentration of alkali and/or alkaline-earth metal salts dissolved therein of at least $10^{-1}$ equivalent/liter; wherein said contacting is effected at a temperature sufficient to allow the removal of said cell residues and microgels without substantially hydrolysing the xanthan gum; whereby the viscosity of said aqueous dispersion is not substantially decreased.

2. A process according to claim 1, wherein said contacting is effected at a pH from 3 to 6.

3. A process according to claim 1 wherein the impure xanthan gum dispersion is a fermentation broth of a xanthan gum-producing bacteria, said gum, containing bacterial cell residues, having not been subjected to a treatment for isolating it in a solid state.

4. A process according to claim 1 wherein the impure xanthan gum is a xanthan gum in a solid state, containing bacterial cell residues.

5. A process according to claim 1, wherein the xanthan gum is an inactive xanthan gum.

6. A process according to claim 1, wherein the enzyme preparation is a Basidiomycetes Poria cellulose preparation.

7. A process according to claim 1, wherein said contacting is effected at a temperature from 25° to 65° C.

8. A process according to claim 3 wherein said temperature from 40° to 60° C.

9. A process according to claim 1, wherein the maximum temperature of said contacting is determined by the empirical formula:

$$T^x = 125 + 43 \log \mu$$

in the case of monovalent metals, μ being the ionic strength.

10. A process according to claim 1, wherein the aqueous dispersion of purified xanthan gum is subjected to a subsequent treatment for precipitating the gun, the precipitated gum is separated as a solid and dried, and the dry, solid purified gum is recovered.

11. A process according to claim 1, wherein the enzyme preparation is a Basidiomycetes Polyporaceae cellulose preparation.

12. A process according to claim 11, wherein the enzyme preparation is a Basiodiomycetes Polyporus cellulose preparation.

13. A process according to claim 11, wherein the enzyme preparation is a Basidiomycetes Trametes cellulose preparation.

14. A process according to claim 11, wherein the enzyme preparation is a Basidiomycetes cellulase preparation from the genus Collybia, Lentinus, Pleurotus, Schizophyllum, Fistulina or Fomes.

* * * * *

UNITED STATES PATENT AND TRADEMARK OFFICE
CERTIFICATE OF CORRECTION

PATENT NO. : 4,416,990

DATED : November 22, 1983

INVENTOR(S) : Marguerite Rinaudo et al

It is certified that error appears in the above-identified patent and that said Letters Patent is hereby corrected as shown below:

Title page, line 3: reads "FILTRABHILITY OF XANTHAN GUMS"
should read -- FILTRABILITY OF XANTHAN GUMS -- .

Column 1, line 3: reads "FILTRABHILITY OF XANTHAN GUMS"
should read -- FILTRABILITY OF XANTHAN GUMS -- .

Column 2, line 41: reads "fied solution of xantan gum, through one or more cali-"
should read --fied solution of xanthan gum, through one or more cali- -- .

Column 3, line 28: reads "depolymerization. It has been established in article of D."
should read --depolymerization. It has been established in the article of D.--.

Column 4, line 59: reads "are which can be used directly, after dilution at the"
should read -- are obtained which can be used directly, after dilution at the -- .

Column 5, line 27: reads "mycetes, particuarly fungi pertaining tothe Aspergillus"
should read -- mycetes, particularly fungi pertaining to the Aspergillus --.

Column 7, line 51: reads "ions as well as for mixtures or monovalent ions with"
should read --ions as well as for mixtures of monovalent ions with -- .

Column 8, line 31: reads "must not in any manner be considered as limited the"
should read -- must not in any manner be considered as limiting the -- .

UNITED STATES PATENT AND TRADEMARK OFFICE
CERTIFICATE OF CORRECTION

PATENT NO. : 4,416,994
DATED : November 22, 1983
INVENTOR(S) : Walter M. Nakatsukasa, Jeffrey T. Fayerman, James A. Mabe It is certified that error appears in the above—identified patent and that said Letters Patent is hereby corrected as shown below:

In column 4, line 23, delete the first listed "pBR324".

In column 4, line 65, "IS. tenebrarius" should be changed to -- S. tenebrarius --.

In column 5, line 30, "(alnkacidin, borrelidin)" should be changed to -- (lankacidin, borrelidin) --.

In column 9, line 4, "11 1. 11." should be changed to -- 1.11. --.

In column 18, line 68, "pEL7.5" should be changed to -- pEL7.6 --.

Signed and Sealed this

Twenty-third Day of April 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,416,999                        Page 1 of 2

DATED : November 22, 1983

INVENTOR(S) : HIROMI FUKUOKA, MASATAKA MATSUO, KAZUO HAMAI, TOKUAKI HATTA and MITUO SUGAWARA It is certified that error appears in the above—identified patent and that said Letters Patent is hereby corrected as shown below:

Title page, left hand column, line 2, change "Hiromi et al." to read "Fukuoka et al.".

Title page, left hand column, the section designated "[75] Inventors:", change "Fukuoka Hiromi" to read "Hiromi Fukuoka".

Signed and Sealed this

Twenty-first Day of August 1984

[SEAL]

Attest:

GERALD J. MOSSINGHOFF

Attesting Officer      Commissioner of Patents and Trademarks

UNITED STATES PATENT AND TRADEMARK OFFICE
CERTIFICATE OF CORRECTION

PATENT NO. : 4,416,999　　　　　　　　　　　Page 2 of 2

DATED : November 22, 1983

INVENTOR(S) : Hiromi Fukuoka, Masataka Matsuo, Kazuo Hamai, Tokuaki Hatta and Mituo Sugawara It is certified that error appears in the above-identified patent and that said Letters Patent is hereby corrected as shown below:

At the bottom of the title page, cancel the figure of drawing set forth and insert therefor, the following: